(12) United States Patent
Huser

(10) Patent No.: US 12,708,739 B2
(45) Date of Patent: Aug. 18, 2026

(54) DRAINAGE SPIGOT GUARD

(71) Applicant: Amy Huser, Noblesville, IN (US)

(72) Inventor: Amy Huser, Noblesville, IN (US)

(73) Assignee: Spigot Guard LLC, Noblesville, IN (US)

( * ) Notice: Subject to any disclaimer, the term of this patent is extended or adjusted under 35 U.S.C. 154(b) by 369 days.

(21) Appl. No.: 18/388,186

(22) Filed: Nov. 8, 2023

(65) Prior Publication Data

US 2024/0149014 A1 May 9, 2024

Related U.S. Application Data

(60) Provisional application No. 63/382,815, filed on Nov. 8, 2022.

(51) Int. Cl.
*A61M 25/00* (2006.01)
*A61M 25/01* (2006.01)

(52) U.S. Cl.
CPC ..... *A61M 25/0017* (2013.01); *A61M 25/0111* (2013.01); *A61M 2210/1078* (2013.01)

(58) Field of Classification Search
CPC .......... A61M 25/0017; A61M 25/0111; A61M 2210/1078; A61M 2025/0056; A61M 39/16; A61M 39/162; A61M 39/165; A61M 39/20; A61M 2025/0018; A61M 2210/1085; A61M 2025/0019; A61M 2210/1089; A61L 2202/24; A61B 90/70
See application file for complete search history.

(56) References Cited

U.S. PATENT DOCUMENTS 4,810,241 A * 3/1989 Rogers .................. A61M 1/285 604/905
5,554,135 A * 9/1996 Menyhay ............. A61M 39/20 604/539
2002/0143292 A1 10/2002 Flinchbaugh
2004/0123410 A1* 7/2004 Terry .................. A46B 13/008 15/23
2008/0281284 A1 11/2008 Garfield et al.
2010/0063465 A1 3/2010 Hoyte
2011/0009849 A1 1/2011 Christensen et al.
2013/0197485 A1* 8/2013 Gardner ............. A61M 39/162 604/533
2016/0235963 A1 8/2016 McDaniel
2021/0138225 A1* 5/2021 Jiang .................... A61M 39/20

OTHER PUBLICATIONS

International Search Report and Written Opinion issued on Feb. 14, 2024 in International Application No. PCT/US2023/037044.

* cited by examiner

*Primary Examiner* — Guy K Townsend
*Assistant Examiner* — Alessandro R Del Priore
(74) *Attorney, Agent, or Firm* — David Meibos; Maywood IP Law

(57) ABSTRACT

A drainage spigot guard may be configured to disinfect a spigot from a urinary catheter. The drainage spigot guard may include a shell with an interior cavity shaped to receive the spigot. The drainage spigot guard may further include a first disinfectant swab within the interior cavity. The first disinfectant swab may be positioned to disinfect at least part of the spigot in response to insertion of the spigot into the interior cavity. The shell may have an exterior shape configured to be received within a spigot retainer on a urinary catheter bag attached to the spigot.

14 Claims, 15 Drawing Sheets

2000
2200
2300

2000
2200
1400

DRAINAGE SPIGOT GUARD

CROSS-REFERENCE TO RELATED APPLICATIONS

This application claims the benefit of U.S. Provisional Patent Application Ser. No. 63/382,815, filed on Nov. 8, 2022 and entitled DRAINAGE SPIGOT GUARD, which is incorporated by reference as though set forth herein in its entirety.

TECHNICAL FIELD

The present disclosure relates to devices and methods for medical drainage spigot covers, guards and other antiseptic and antimicrobial protective covers. More specifically, the present disclosure relates to devices and methods for drainage spigot guards for urinary catheters.

BACKGROUND

Catheter acquired urinary tract infections (CAUTIs) are among the leading healthcare-associated infections. Complications associated with CAUTIs result in increased length of stay of 2-4 days, patient discomfort, and excess health care costs, and contribute to increased mortality. Research suggests that 36% of all CAUTIs are caused by bacteria entering at the unprotected foley drainage spigot.

A clinical component of reducing CAUTI consists of the proper care and maintenance of the catheter. Currently, clinical practice calls for cleansing the drainage spigot with an alcohol prep pad after emptying the urine bag. However, this practice in the hospital setting relies on the honor system for nurses and techs to perform. All too frequently, this recommended practice is ignored, leading to bacterial entry at the drainage spigot and potential CAUTI.

SUMMARY

The various systems and methods of the present disclosure have been developed in response to the present state of the art, and in particular, in response to the problems and needs in the art that have not yet been fully solved by currently available devices and methods for drainage spigot guards.

In some embodiments, a drainage spigot guard may be configured to disinfect a spigot from a urinary catheter. The drainage spigot guard may have a shell with an interior cavity shaped to receive the spigot and a first disinfectant swab within the interior cavity. The first disinfectant swab may be positioned to disinfect at least part of the spigot in response to insertion of the spigot into the interior cavity. The shell may have an exterior shape configured to be received within a spigot retainer on a urinary catheter bag attached to the spigot.

In the drainage spigot guard of any preceding paragraph, the drainage spigot guard may further include a second disinfectant swab within the interior cavity.

In the drainage spigot guard of any preceding paragraph, the first disinfectant swab may be annular shaped.

In the drainage spigot guard of any preceding paragraph, the first disinfectant swab may be positioned to disinfect an exterior surface of the spigot in response to insertion of the spigot into the interior cavity.

In the drainage spigot guard of any preceding paragraph, the first disinfectant swab may be cylindrical shaped.

In the drainage spigot guard of any preceding paragraph, the first disinfectant swab may be positioned to disinfect an interior surface of the spigot in response to insertion of the spigot into the interior cavity.

In the drainage spigot guard of any preceding paragraph, a diameter at a proximal end of the shell may be larger than a diameter at a distal end of the shell.

In the drainage spigot guard of any preceding paragraph, the shell may have an opening and a seal positioned to cover the opening.

In the drainage spigot guard of any preceding paragraph, the first disinfectant swab may have an inside portion configured to receive a post formed in the shell.

In the drainage spigot guard of any preceding paragraph, the first disinfectant swab may have a stem configured to be received in a recess formed in the shell.

In the drainage spigot guard of any preceding paragraph, a diameter at a proximal end of the first disinfectant swab may be larger than a diameter at a distal end of the first disinfectant swab.

In the drainage spigot guard of any preceding paragraph, the shell may be configured to be received in a spigot retainer of a urinary catheter bag such that, with the shell on a spigot, locking arms secure the spigot to the spigot retainer.

In some embodiments, a drainage spigot guard may be configured to disinfect a spigot from a urinary catheter. The drainage spigot guard may have a shell with an interior cavity shaped to receive the spigot, a first disinfectant swab within the interior cavity, and a second disinfectant swab within the interior cavity. The first disinfectant swab may be positioned to disinfect an exterior surface of the spigot in response to insertion of the spigot into the interior cavity. The second disinfectant swab may be positioned to disinfect an interior surface of the spigot in response to insertion of the spigot into the interior cavity.

In the drainage spigot guard of any preceding paragraph, the shell further may have an opening and a seal positioned to cover the opening.

In the drainage spigot guard of any preceding paragraph, the first disinfectant swab may be annular shaped.

In the drainage spigot guard of any preceding paragraph, the second disinfectant swab may be cylindrical shaped.

In the drainage spigot guard of any preceding paragraph, a diameter at a proximal end of the shell may be larger than a diameter at a distal end of the shell.

In the drainage spigot guard of any preceding paragraph, the second disinfectant swab may have an inside portion configured to receive a post formed in the shell.

In the drainage spigot guard of any preceding paragraph, a diameter at a proximal end of the first disinfectant swab may be larger than a diameter at a distal end of the first disinfectant swab.

In the drainage spigot guard of any preceding paragraph, the shell may be configured to be received in a spigot retainer of a urinary catheter bag such that, with the shell on a spigot, locking arms secure the spigot to the spigot retainer.

In some embodiments, a drainage spigot guard may be configured to disinfect a spigot from a urinary catheter. The drainage spigot guard may have a shell with an opening and an interior cavity that may be accessible through the opening and may be shaped to receive the spigot. The drainage spigot may further include a seal positioned to cover the opening and a first disinfectant swab within the interior cavity, adjacent to the opening and the seal. The first disinfectant swab may be positioned to disinfect an exterior surface of the spigot in response to insertion of the spigot into the interior cavity.

In the drainage spigot guard of any preceding paragraph, the seal may have a pull tab.

In the drainage spigot guard of any preceding paragraph, the shell may have a flange at a proximal end to facilitate attachment of the seal.

In some embodiments, a method for securing a drainage spigot guard to a catheter may include: disengaging a drainage spigot from a spigot retainer attached to a urinary catheter, draining a urinary catheter bag into an appropriate receptacle, advancing a spigot distal end of the drainage spigot into an interior cavity of the drainage spigot guard until the drainage spigot is fully seated within the drainage spigot guard, and advancing the drainage spigot with the drainage spigot guard into the spigot retainer until locking arms of the drainage spigot engage the spigot retainer.

These and other features and advantages of the present disclosure will become more fully apparent from the following description and appended claims or may be learned by the practice of the implants, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

Figure 1A:
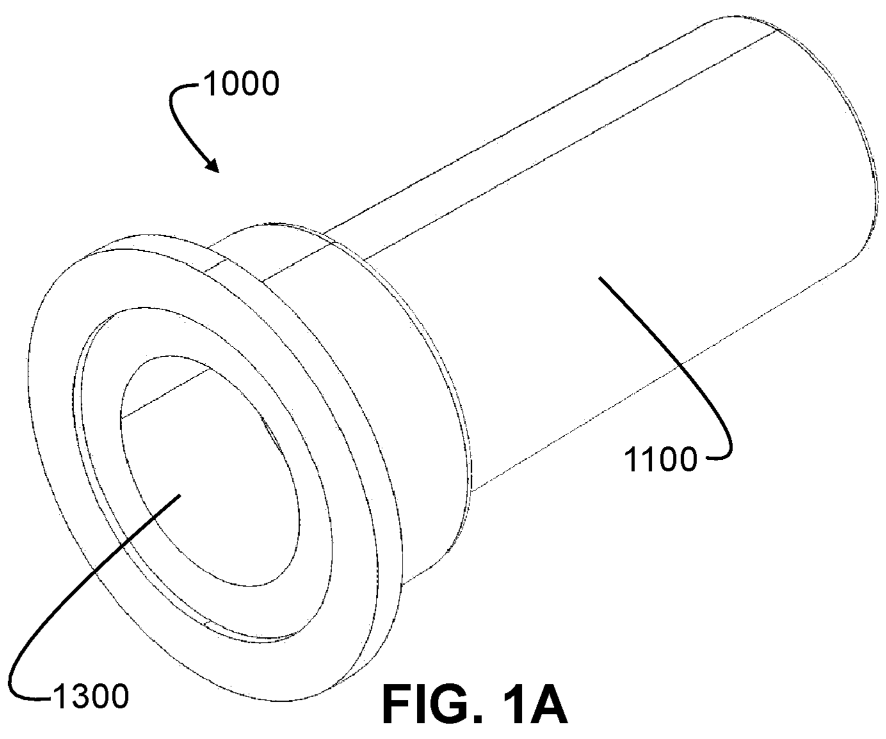
FIG. 1A is a perspective view of a drainage spigot guard according to an embodiment.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The present disclosure relates to devices and methods for medical drainage spigot covers, guards and other antiseptic and antimicrobial protective covers. More specifically, the present disclosure relates to devices and methods for drainage spigot guards for urinary catheters. Those skilled in the art will recognize that the following description is merely illustrative of the principles of the technology, which may be applied in various ways to provide many alternative embodiments. The present disclosure illustrates a drainage spigot guard applied to a urinary catheter for the purposes of illustrating the concepts of the present design. However, it will be understood that other variations and uses are contemplated including, but not limited to, catheters, luer connectors, needless connectors, access ports, syringes, and other medical tubing and connectors.

Figure 1B:
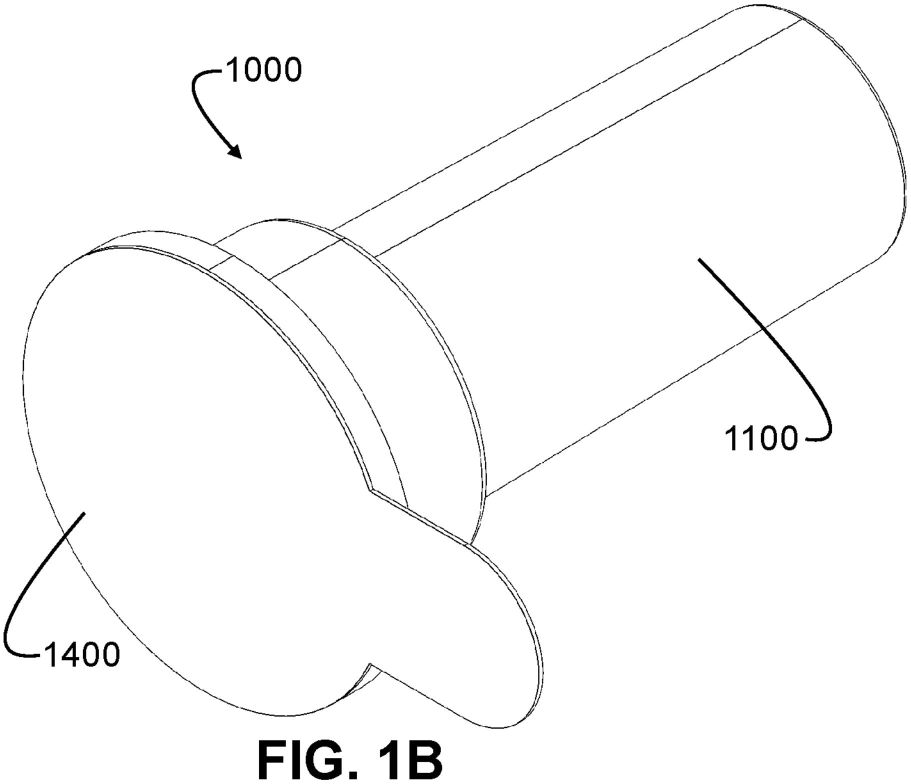
FIG. 1B is a perspective view of the drainage spigot guard of FIG. 1A with a seal according to an embodiment.

FIG. 1A is a perspective view of a drainage spigot guard 1000 according to an embodiment. FIG. 1B is a perspective view of the drainage spigot guard 1000 with a seal 1400. The drainage spigot guard 1000 may be configured to provide both a bacterial barrier and an aseptic cleanse for care and maintenance of a urinary catheter bag 3000, more specifically, a drainage spigot 3010 of a urinary catheter bag 3000. The drainage spigot guard 1000 may further be configured to reduce the risk of infection at a vulnerable point of bacterial entry in the urinary catheter system.

Figures 2A, 2B:
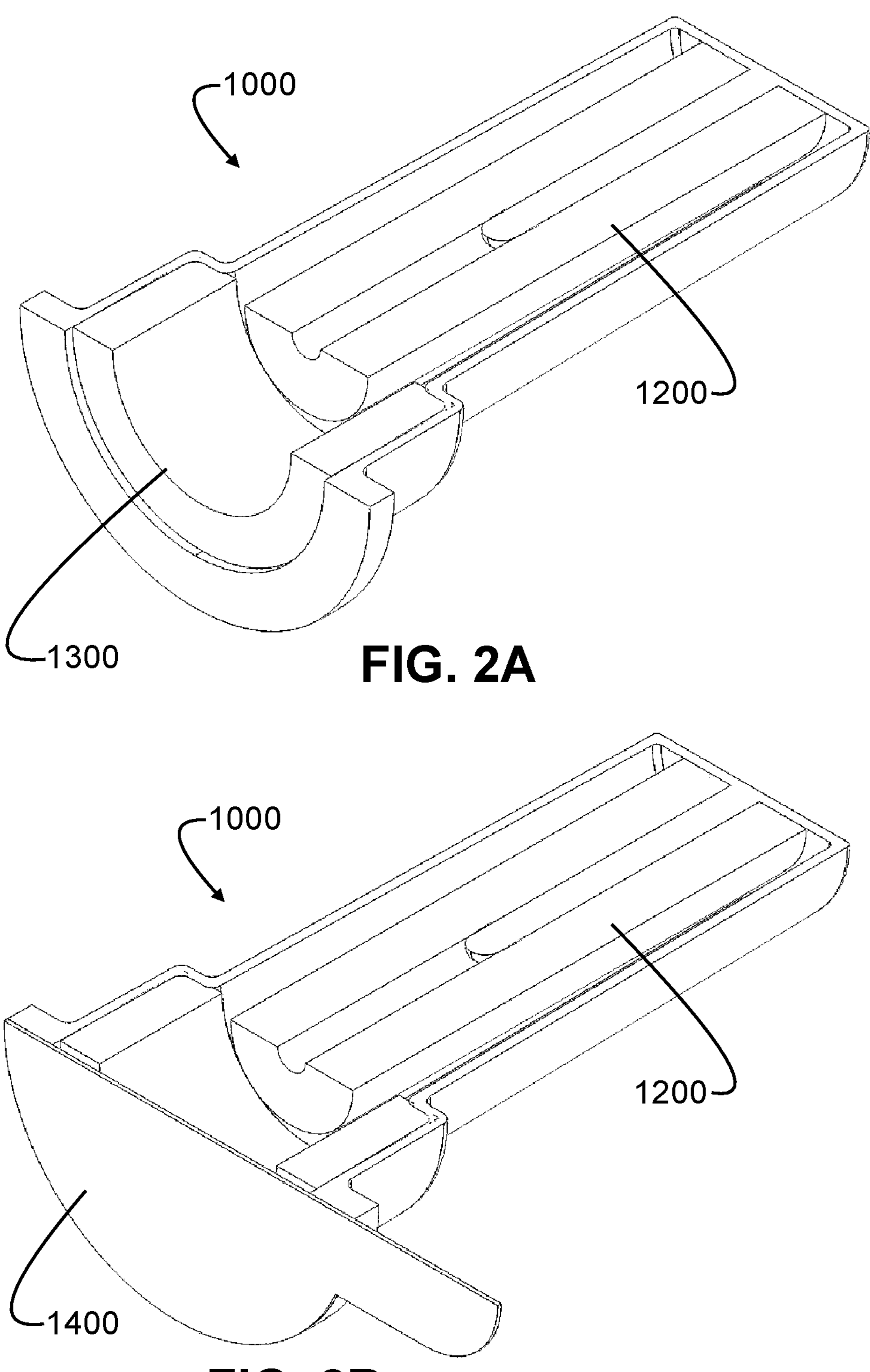
FIG. 2A is a perspective section view of the drainage spigot guard of FIG. 1A.
FIG. 2B is a perspective section view of the drainage spigot guard with seal of FIG. 1B.

The drainage spigot guard 1000 may include a shell 1100, a first disinfectant swab 1300, a second disinfectant swab 1200, and a seal 1400. FIG. 2A is a perspective section view of the drainage spigot guard 1000 and FIG. 2B is a perspective section view of the drainage spigot guard 1000 with seal 1400. The drainage spigot guard 1000 may be configured so that second disinfectant swab 1200 and the first disinfectant swab 1300 may be within the shell 1100.

Figures 3A, 3B:
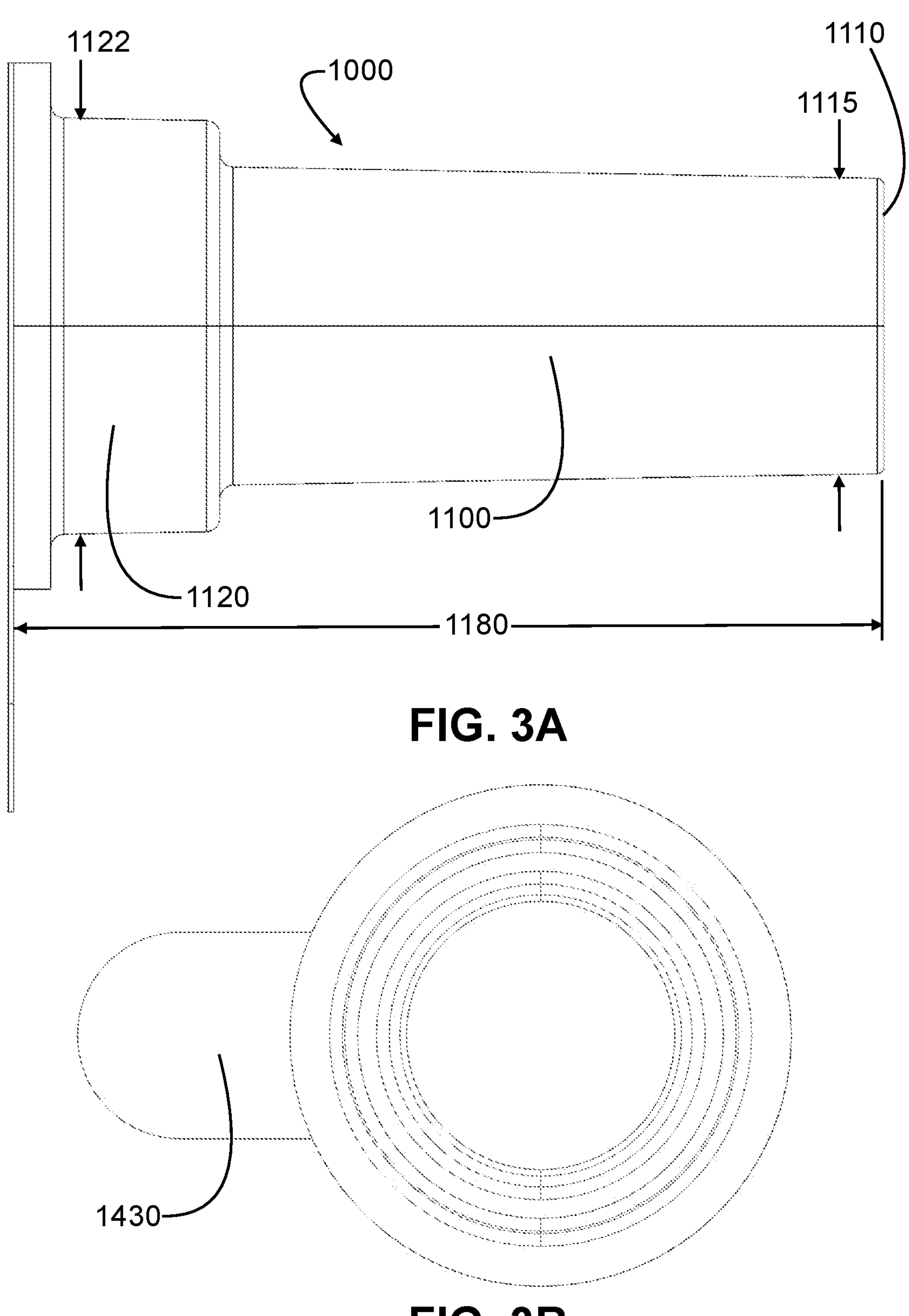
FIG. 3A is a front view of the drainage spigot guard with seal of FIG. 1B.
FIG. 3B is an end view of the drainage spigot guard with seal of FIG. 1B.

FIG. 3A is a front view of the drainage spigot guard 1000 with seal 1400 and FIG. 3B is an end view of the drainage spigot guard 1000 with seal 1400. The shell 1100 may include a distal end 1110, a proximal end 1120, and a length 1180 there between. The distal end 1110 may include a distal exterior diameter 1115 and the proximal end 1120 may include a proximal exterior diameter 1122. The shell 1100 may be configured so that a proximal exterior diameter 1122 at the proximal end 1120 of the shell 1100 is larger than a distal exterior diameter 1115 at the distal end 1110 of the shell 1100. The shell 1100 may further include an opening 1125 and an interior cavity 1195, accessible through the opening 1125 and shaped to receive a drainage spigot 3010. The shell 1100 may have an exterior shape configured to be received within a spigot retainer 3020 on a urinary catheter bag 3000 attached to a drainage spigot 3010. More specifically, the shell 1100 may have a diameter of 9 mm to 13 mm, preferably 11 mm at the distal end 1110, a diameter of 12 mm to 18 mm, preferably 15 mm at the proximal end 1120, and a length 1180 of 20 mm to 35 mm, preferably 28 mm. The interior cavity 1195 may be shaped to receive a drainage spigot 3010. More specifically, the interior cavity 1195 may have a diameter of 9 mm to 11 mm, preferably 10 mm at the distal end 1110 and a diameter of 13 mm to 15 mm, preferably 14 mm at the opening 1125. The exterior shape of the shell 1100 may include grooves, ridges, or a surface texture configured to improve a grip of the drainage spigot guard 1000 during insertion and/or withdrawal of a drainage spigot 3010.

Figures 4A, 4B:
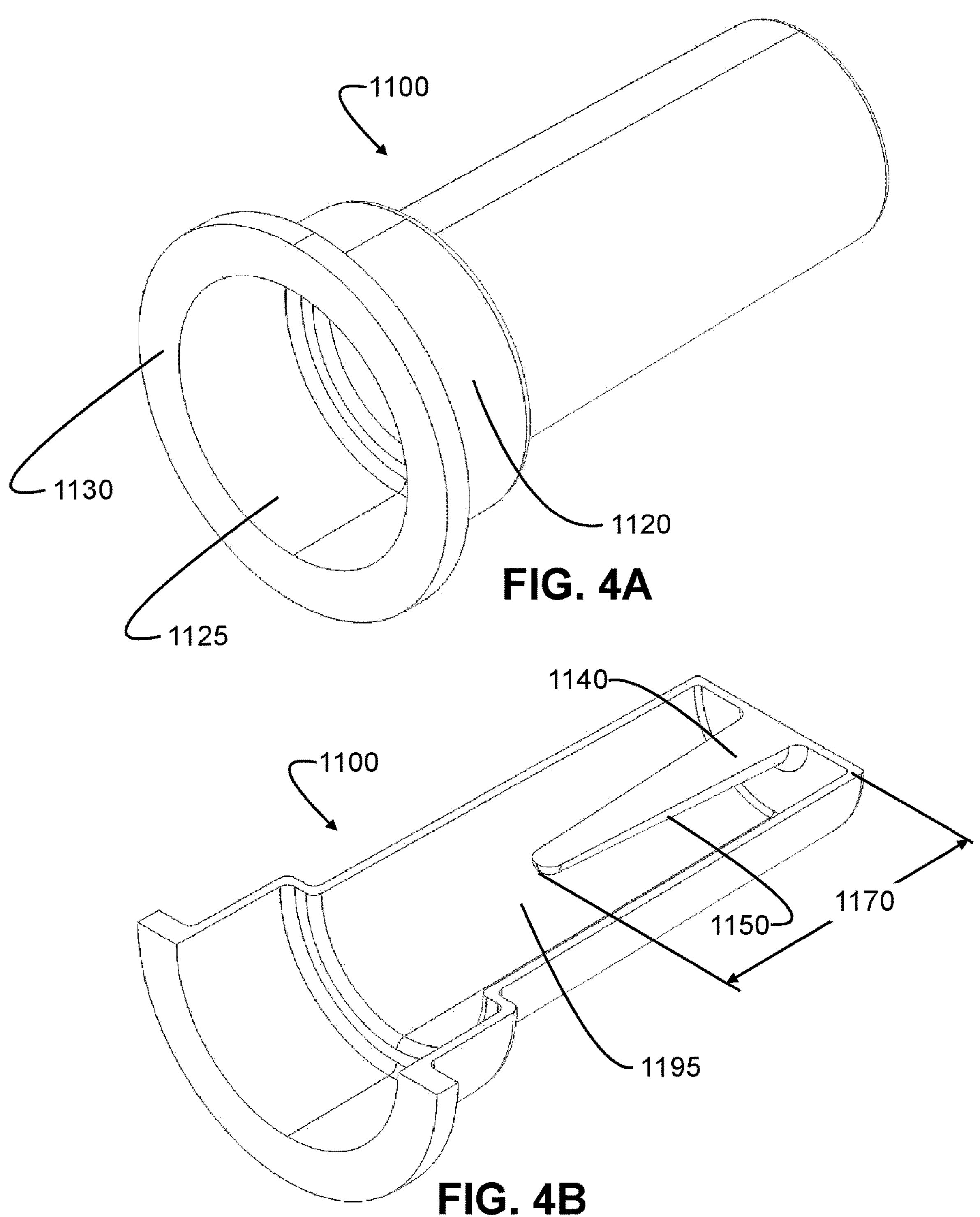
FIG. 4A is a perspective view of a shell of the drainage spigot guard of FIG. 1A according to an embodiment.
FIG. 4B is a perspective section view of the shell of FIG. 4A.

FIG. 4A is a perspective view of a shell 1100 of a drainage spigot guard 1000 according to an embodiment. FIG. 4B is a perspective section view of the shell 1100. The shell 1100 may have an interior cavity 1195 including a mounting post 1140. The mounting post 1140 may be configured to retain a second disinfectant swab 1200 within the interior cavity 1195 and may include a mounting post outer portion 1150 and a mounting post length 1170. Additionally, the drainage spigot guard 1000 and the mounting post 1140 may be configured to retain the second disinfectant swab 1200 during insertion and withdrawal of a drainage spigot 3010.

The mounting post outer portion 1150 may be generally circular and may have a taper along at least a portion of the mounting post length 1170 wherein a diameter at the distal end is greater than a diameter at the proximal end. The mounting post outer portion 1150 may further be configured so that a cross-sectional area at the distal end of the mounting post outer portion 1150 is greater than a cross-sectional area of an inside portion 1210 of a second disinfectant swab 1200. The mounting post outer portion 1150 may be configured so that the mounting post length 1170 is less than or equal to the length 1230 of the second disinfectant swab 1200.

Alternately, the mounting post outer portion 1150 may be generally cylindrical and may have generally the same diameter along the mounting post length 1170. Alternately, the mounting post outer portion 1150 may have a non-circular cross-section. The mounting post outer portion 1150 may further be configured so that cross-sectional area is greater than or equal to the cross-sectional area of an inside portion 1210 of a second disinfectant swab 1200. The mounting post outer portion 1150 may have ridges, grooves, barbs, or a surface treatment to secure a second disinfectant swab 1200 to the mounting post 1140 during insertion and withdrawal of a drainage spigot 3010. Alternatively, or additionally, the second disinfectant swab 1200 may be secured to the mounting post 1140 using an adhesive.

The shell 1100 may further include a flange 1130 at the opening 1125. The seal 1400 may be configured to be positioned to cover the opening 1125. The flange 1130 may be configured to receive the seal 1400 wherein the engagement of the seal 1400 with the flange 1130 may provide a sterile barrier for the interior cavity 1195 of the shell 1100, a first disinfectant swab 1300, and a second disinfectant swab 1200.

Figure 5A:
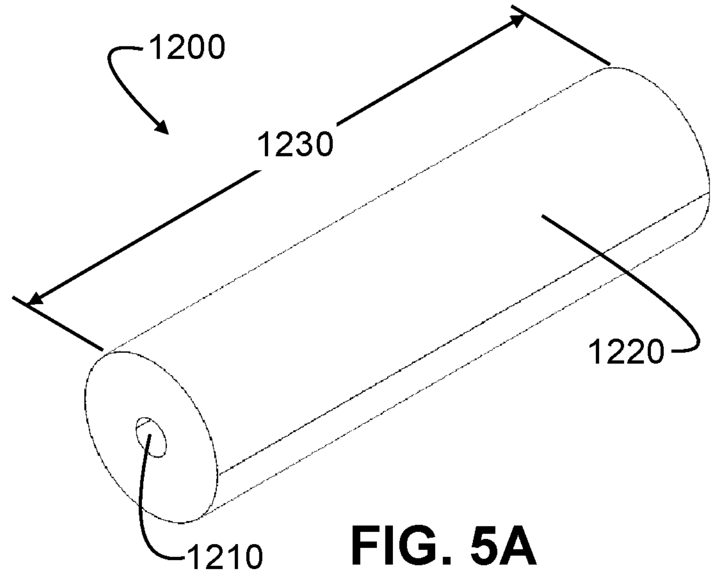
FIG. 5A is a perspective view of a second disinfectant swab of the drainage spigot guard of FIG. 1A according to an embodiment.

FIG. 5A is a perspective view of a second disinfectant swab 1200 of the drainage spigot guard 1000 according to an embodiment. The second disinfectant swab 1200 may be configured to be coupled to a shell 1100 within an interior cavity 1195 of the drainage spigot guard 1000. The second disinfectant swab 1200 may be positioned to disinfect an interior surface 3050 of a drainage spigot 3010 in response to insertion of the drainage spigot 3010 into the interior cavity 1195 of the drainage spigot guard 1000.

The second disinfectant swab 1200 may be manufactured from an absorbent polyurethane impregnated with approximately 0.5 milliliters of a liquid disinfectant such as isopropyl alcohol having a concentration between 50% and 99%, preferably 70%. Alternate disinfectants such as: hydrogen peroxide, ethanol having a concentration between 50% and 95%, chlorhexidine, alcohols, or a combination of disinfectants may be used. The second disinfectant swab 1200 may be impregnated with a disinfectant through soaking, injection or other suitable means. Alternatively, the second disinfectant swab 1200 may be manufactured from open pore thermoplastic polymers, synthetic fibers, or a combination of materials.

The second disinfectant swab 1200 may include an inside portion 1210, an outside portion 1220, and a length 1230. The second disinfectant swab 1200 may be at least partially cylindrical shaped. The inside portion 1210 may be configured to receive a mounting post 1140 of a shell 1100. The outside portion 1220 may be configured to be received within an interior surface 3050 of a drainage spigot 3010. The outside portion 1220 may be generally cylindrical and may have a diameter greater than or equal to a diameter of an interior surface 3050 of a drainage spigot 3010. More specifically, the outside portion 1220 may have a diameter between 6 mm and 8 mm, preferably 7 mm.

Figure 5B:
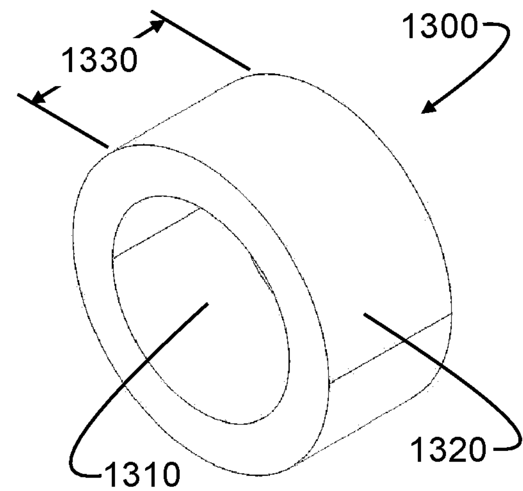
FIG. 5B is a perspective view of a first disinfectant swab of the drainage spigot guard of FIG. 1A according to an embodiment.

FIG. 5B is a perspective view of a first disinfectant swab 1300 of the drainage spigot guard 1000 according to an embodiment. The first disinfectant swab 1300 may be configured to be coupled to a shell 1100 within an interior cavity 1195 of the drainage spigot guard 1000. The first disinfectant swab 1300 may be positioned to disinfect at least part of the drainage spigot 3010 in response to insertion of the drainage spigot 3010 into the interior cavity 1195. The first disinfectant swab 1300 may be positioned to disinfect an exterior surface 3040 of a drainage spigot 3010 in response to insertion of the drainage spigot 3010 into the interior cavity 1195 of the drainage spigot guard 1000.

The first disinfectant swab 1300 may be manufactured from an absorbent polyurethane impregnated with approximately 0.2 milliliters of a liquid disinfectant such as isopropyl alcohol having a concentration between 50% and 99%, preferably 70%. Alternate disinfectants such as: hydrogen peroxide, ethanol having a concentration between 50% and 95%, chlorhexidine, alcohols, or a combination of disinfectants may be used. The first disinfectant swab 1300 may be impregnated with a disinfectant through soaking, injection or other suitable means. Alternatively, the first disinfectant swab 1300 may be manufactured from open pore thermoplastic polymers, synthetic fibers, or a combination of materials.

The first disinfectant swab 1300 may include an inside portion 1310, an outside portion 1320, and a length 1330. The first disinfectant swab 1300 may be annular shaped. The outside portion 1320 may be configured to be received within an interior cavity 1195 of a shell 1100 adjacent to an opening 1125 and a seal 1400. The outside portion 1320 may be configured to be secured to the interior cavity 1195 using a medical grade adhesive. The shell 1100 and the first disinfectant swab 1300 may be configured to retain the first disinfectant swab 1300 during insertion and withdrawal of a drainage spigot 3010. The inside portion 1310 may be generally cylindrical and may have a diameter less than or equal to a diameter of an exterior surface 3040 of a drainage spigot 3010. More specifically, the inside portion 1310 may have a diameter between 8 mm and 10 mm, preferably 9 mm. The length 1330 may be configured so that the first disinfectant swab 1300 is situated within the interior cavity 1195 and does not extend beyond the opening 1125.

Figures 6A, 6B:
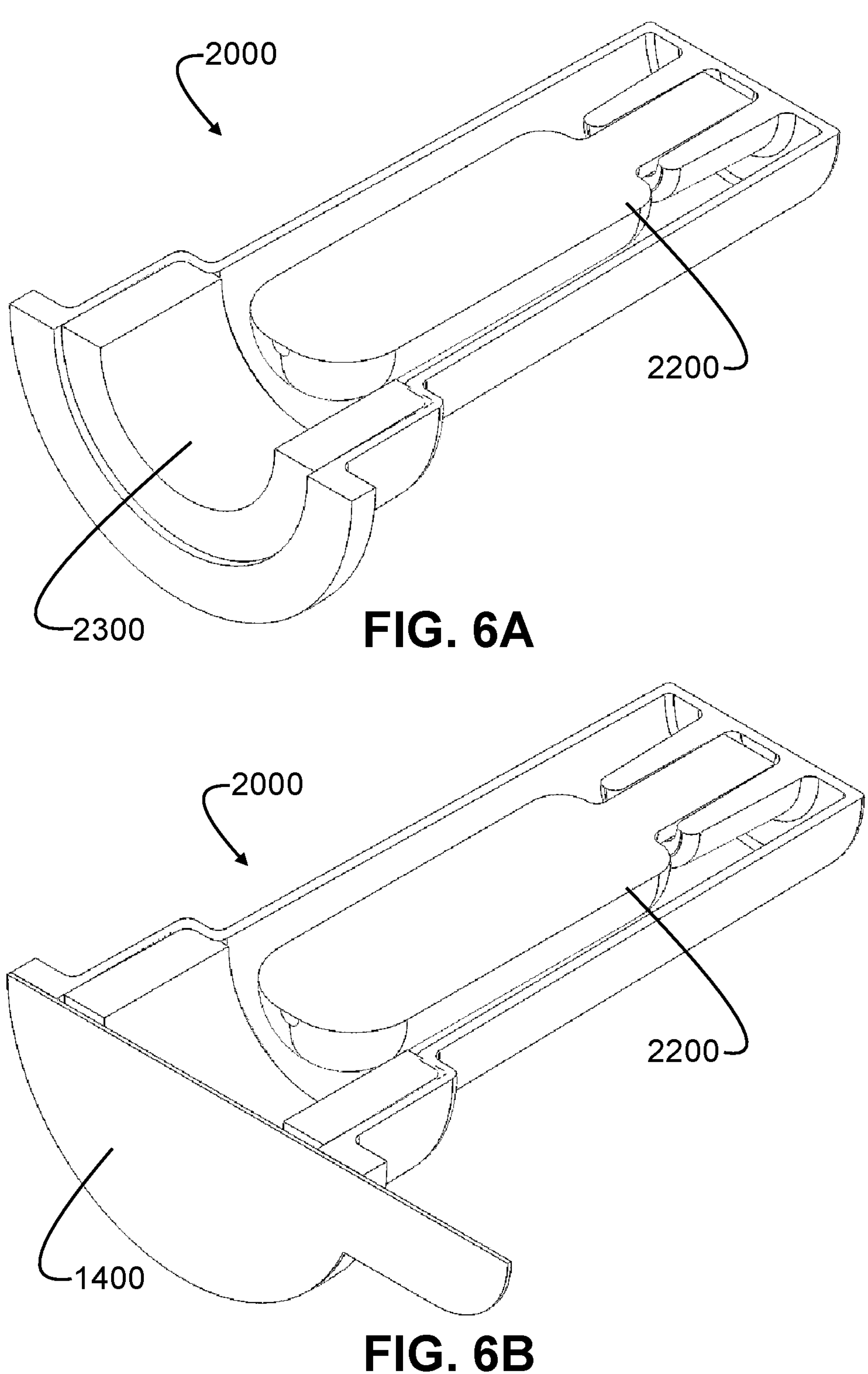
FIG. 6A is a perspective section view of a drainage spigot guard according to another embodiment.
FIG. 6B is a perspective section view of the drainage spigot guard of FIG. 6A with a seal according to an embodiment.

A drainage spigot guard 2000 may include a shell 2100, a first disinfectant swab 2300, a second disinfectant swab 2200, and a seal 1400. FIG. 6A is a perspective section view of the drainage spigot guard 2000 according to another embodiment. FIG. 6B is a perspective section view of the drainage spigot guard 2000 with a seal 1400. The drainage spigot guard 2000 may be configured so that second disinfectant swab 2200 and the first disinfectant swab 2300 may be within the shell 2100.

Figures 7A, 7B:
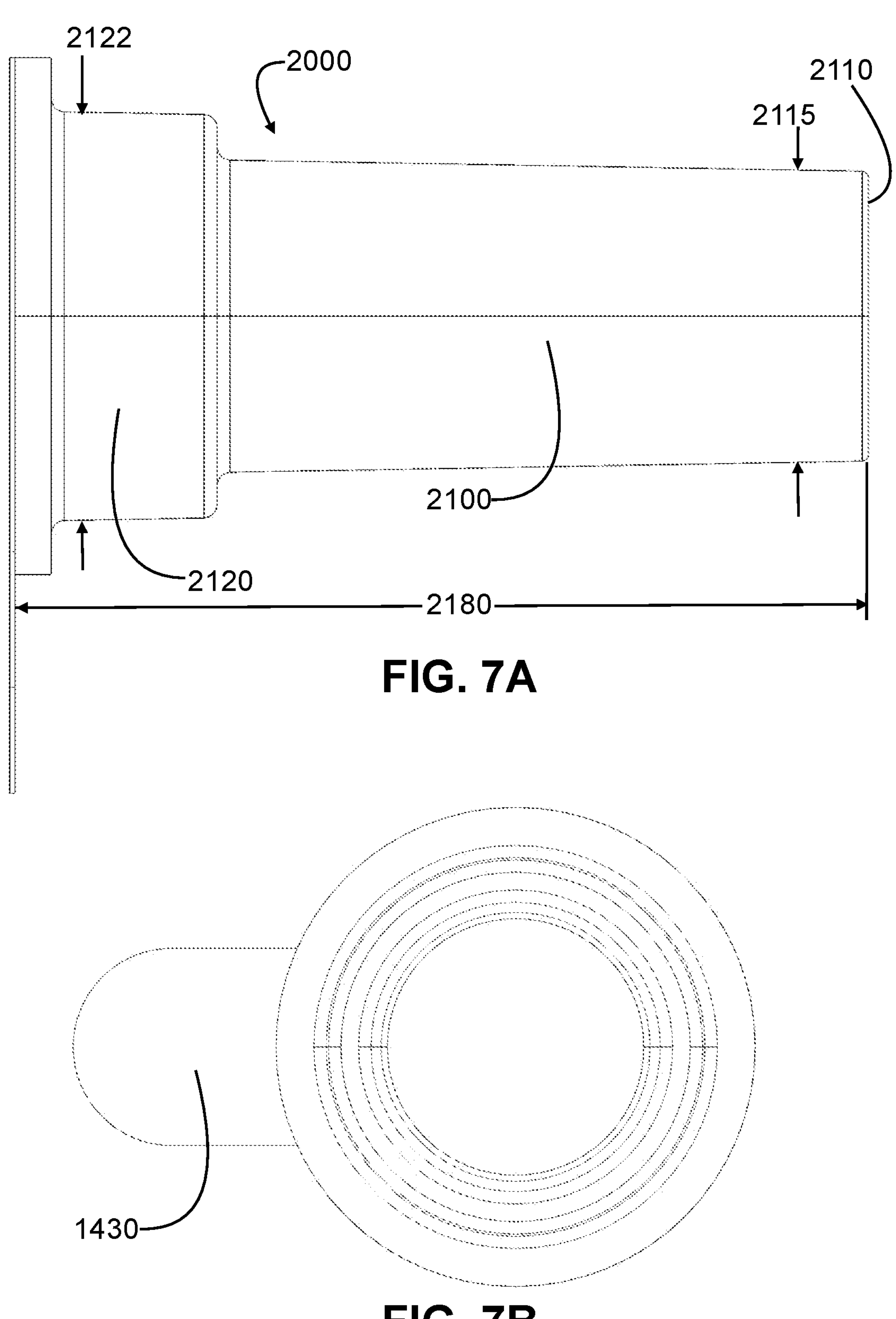
FIG. 7A is a front view of the drainage spigot guard with seal of FIG. 6B.
FIG. 7B is an end view of the drainage spigot guard with seal of FIG. 6B.

FIG. 7A is a front view of the drainage spigot guard 2000 with seal 1400 and FIG. 7B is an end view of the drainage spigot guard 2000 with seal 1400. The shell 2100 may include a distal end 2110, a proximal end 2120, and a length 2180 there between. The distal end 2110 may include a distal exterior diameter 2115 and the proximal end 2120 may include a proximal exterior diameter 2122. The shell 2100 may be configured so that a proximal exterior diameter 2122 at the proximal end 2120 of the shell 2100 is larger than a distal exterior diameter 2115 at the distal end 2110 of the shell 2100. The shell 2100 may further include an opening 2125 and an interior cavity 2195, accessible through the opening 2125 and shaped to receive a drainage spigot 3010. The shell 2100 may have an exterior shape configured to be received within a spigot retainer 3020 on a urinary catheter bag 3000 attached to a drainage spigot 3010. More specifically, the shell 2100 may have a diameter of 9 mm to 13 mm, preferably 11 mm at the distal end 2110, a diameter of 12 mm to 18 mm, preferably 15 mm at the proximal end 2120, and a length 1180 of 20 mm to 35 mm, preferably 28 mm. The interior cavity 2195 may be shaped to receive a drainage spigot 3010. More specifically, the interior cavity 2195 may have a diameter of 9 mm to 11 mm, preferably 10 mm at the distal end 1110 and a diameter of 13 mm to 15 mm, preferably 14 mm at the opening 2125. The exterior shape of the shell 2100 may include grooves, ridges, or a surface texture configured to improve a grip of the drainage spigot guard 1000 during insertion and/or withdrawal of a drainage spigot 3010.

Figures 8A, 8B:
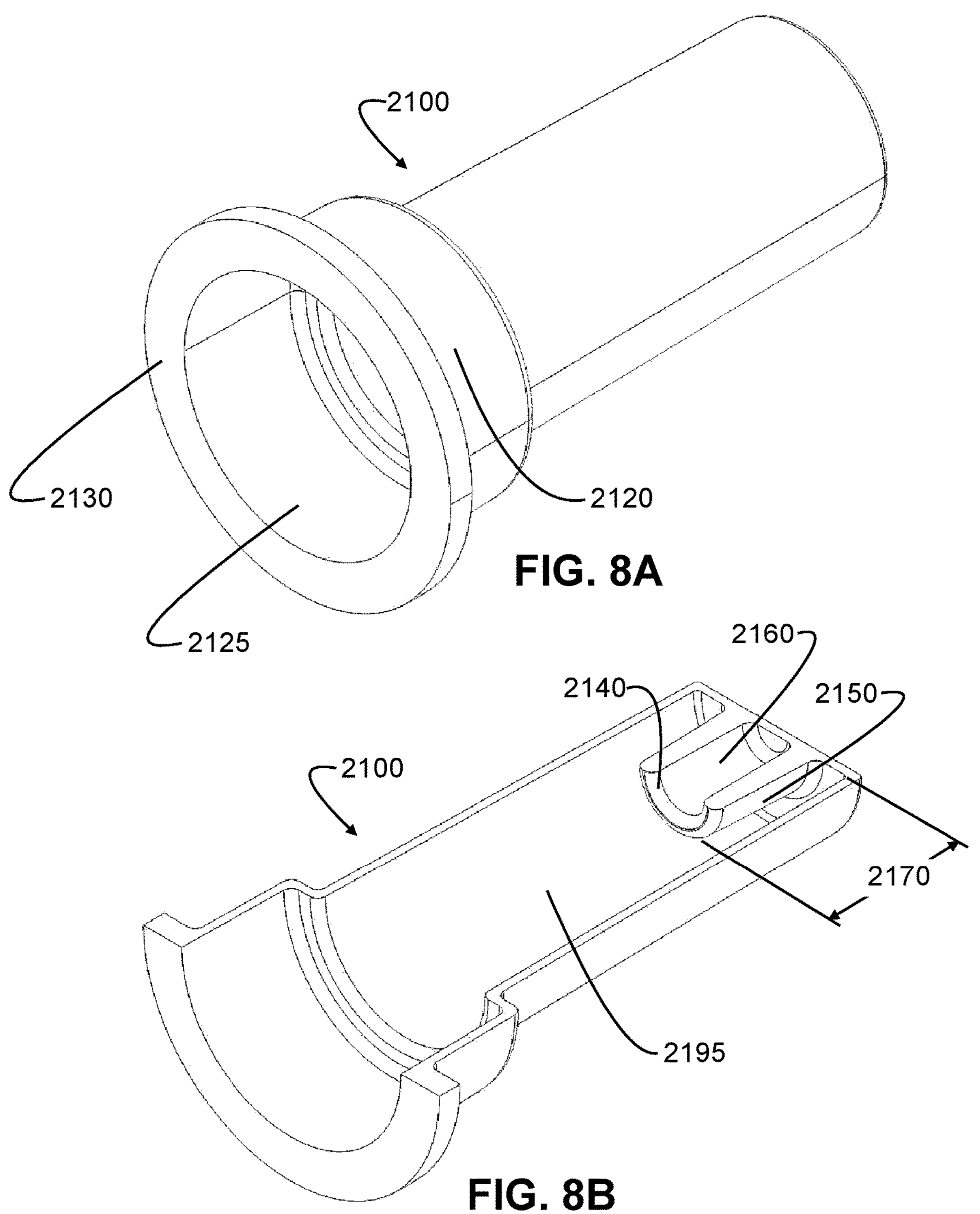
FIG. 8A is a perspective view of a shell of the drainage spigot guard of FIG. 6A according to an embodiment.
FIG. 8B is a perspective section view of the shell of FIG. 8A.

FIG. 8A is a perspective view of a shell 2100 of a drainage spigot guard 2000 according to an embodiment. FIG. 8B is a perspective section view of the shell 2100. The shell 2100 may have an interior cavity 2195 including a recess 2140. The recess 2140 may be configured to retain a second disinfectant swab 2200 within the interior cavity 2195 and may include a recess outer portion 2150, a recess inner portion 2160, and a recess length 2170. Additionally, the drainage spigot guard 2000 and the recess 2140 may be configured to retain the second disinfectant swab 2200 during insertion and withdrawal of a drainage spigot 3010.

The recess inner portion 2160 may be generally circular along the recess length 2170. Alternately, the recess inner portion 2160 may have a non-circular cross-section. The recess inner portion 2160 may further be configured so that cross-sectional area is less than or equal to the cross-sectional area of a stem 2240 of a second disinfectant swab 2200. The recess inner portion 2160 may have ridges, grooves, barbs, or a surface treatment to secure a second disinfectant swab 2200 to the recess 2140 during insertion and withdrawal of a drainage spigot 3010. Alternatively, or additionally, the second disinfectant swab 2200 may be secured to the recess 2140 using an adhesive. The recess 2140 may be configured so that the recess length 2170 is less than the length 2230 of the second disinfectant swab 2200. More specifically, the recess length 2170 may be less than or equal to the stem length 2250 of the second disinfectant swab 2200.

The shell 2100 may further include a flange 2130 at the opening 2125. The seal 1400 may be configured to be positioned to cover the opening 2125. The flange 2130 may be configured to receive the seal 1400 wherein the engagement of the seal 1400 with the flange 2130 may provide a sterile barrier for the interior cavity 2195 of the shell 2100, a first disinfectant swab 2300, and a second disinfectant swab 2200.

Figure 9A:
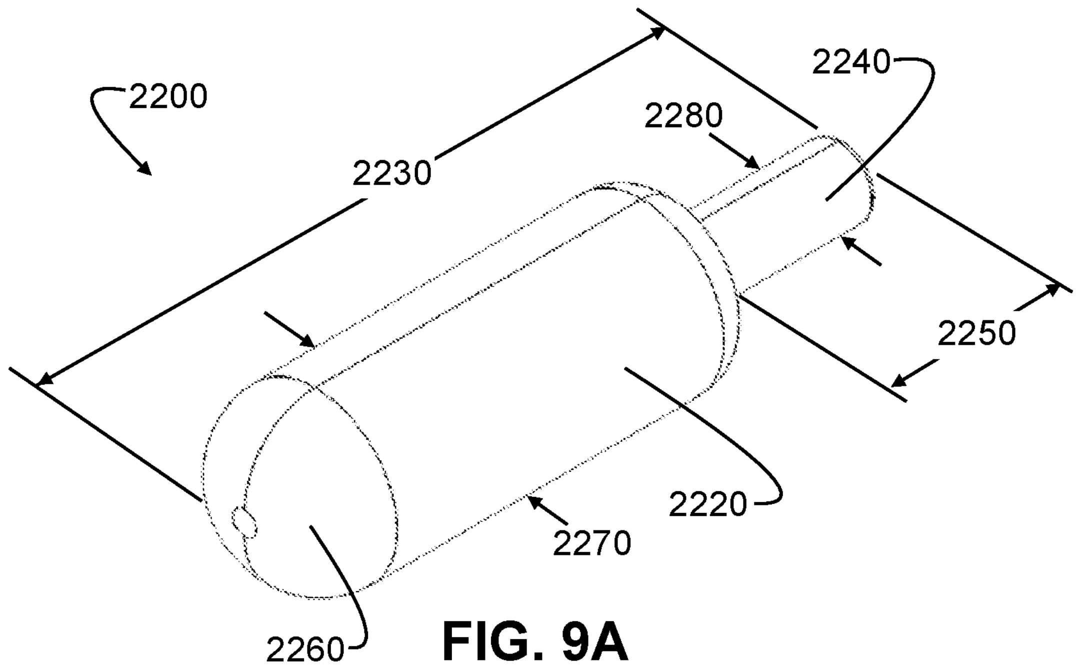
FIG. 9A is a perspective view of a second disinfectant swab of the drainage spigot guard of FIG. 6A according to an embodiment.

FIG. 9A is a perspective view of a second disinfectant swab 2200 of the drainage spigot guard 2000 according to an embodiment. The second disinfectant swab 2200 may be configured to be coupled to a shell 2100 within an interior cavity 2195 of the drainage spigot guard 2000. The second disinfectant swab 2200 may be positioned to disinfect an interior surface 3050 of a drainage spigot 3010 in response to insertion of the drainage spigot 3010 into the interior cavity 2195 of the drainage spigot guard 2000.

The second disinfectant swab 2200 may be manufactured from an absorbent polyurethane impregnated with approximately 0.5 milliliters of a liquid disinfectant such as isopropyl alcohol having a concentration between 50% and 99%, preferably 70%. Alternate disinfectants such as: hydrogen peroxide, ethanol having a concentration between 50% and 95%, chlorhexidine, alcohols, or a combination of disinfectants may be used. The second disinfectant swab 2200 may be impregnated with a disinfectant through soaking, injection or other suitable means. Alternatively, the second disinfectant swab 2200 may be manufactured from open pore thermoplastic polymers, synthetic fibers, or a combination of materials.

The second disinfectant swab 2200 may include an outside portion 2220, a tip 2260, a stem 2240, and a length 1230. The second disinfectant swab 2200 may be at least partially cylindrical shaped. The second disinfectant swab 2200 may include an outside portion 2220 with a proximal diameter 2270 and a stem 2240 with a distal diameter 2280. The proximal diameter 2270 at a proximal end of the second disinfectant swab 2200 may be larger than the distal diameter 2280 at the distal end of the second disinfectant swab 2200. The outside portion 2220 may be configured to be received within an interior surface 3050 of a drainage spigot 3010. The outside portion 2220 may be generally cylindrical and may have a proximal diameter 2270 greater than or equal to a diameter of an interior surface 3050 of a drainage spigot 3010. More specifically, the outside portion 2220 may have a proximal diameter 2270 between 6 mm and 8 mm, preferably 7 mm. The second disinfectant swab 2200 may have a tip 2260 with a radius and/or chamfer configured to guide the second disinfectant swab 2200 into an interior surface 3050 of a drainage spigot 3010.

Figure 9B:
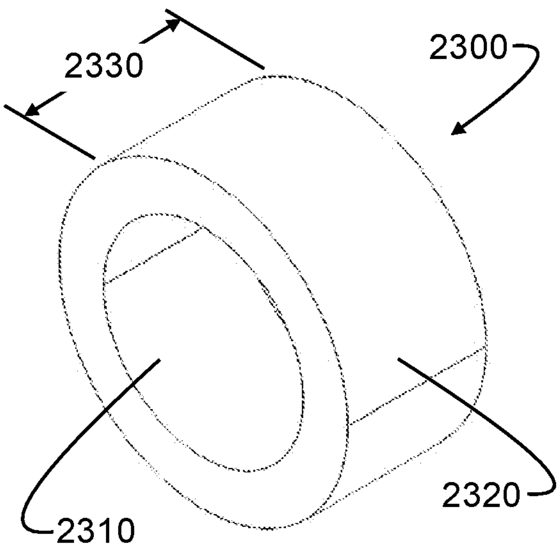
FIG. 9B is a perspective view of a first disinfectant swab of the drainage spigot guard of FIG. 6A according to an embodiment.

FIG. 9B is a perspective view of a first disinfectant swab 2300 of the drainage spigot guard 2000 according to an embodiment. The first disinfectant swab 2300 may be configured to be coupled to a shell 2100 within an interior cavity 2195 of the drainage spigot guard 2000. The first disinfectant swab 2300 may be positioned to disinfect at least part of the drainage spigot 3010 in response to insertion of the drainage spigot 3010 into the interior cavity 2195. The first disinfectant swab 2300 may be positioned to disinfect an exterior surface 3040 of a drainage spigot 3010 in response to insertion of the drainage spigot 3010 into the interior cavity 2195 of the drainage spigot guard 2000.

The first disinfectant swab 2300 may be manufactured from an absorbent polyurethane impregnated with approximately 0.2 milliliters of a liquid disinfectant such as isopropyl alcohol having a concentration between 50% and 99%, preferably 70%. Alternate disinfectants such as: hydrogen peroxide, ethanol having a concentration between 50% and 95%, chlorhexidine, alcohols, or a combination of disinfectants may be used. The first disinfectant swab 2300 may be impregnated with a disinfectant through soaking, injection or other suitable means. Alternatively, the first disinfectant swab 2300 may be manufactured from open pore thermoplastic polymers, synthetic fibers, or a combination of materials.

The first disinfectant swab 2300 may include an inside portion 2310, an outside portion 2320, and a length 2330. The first disinfectant swab 2300 may be annular shaped. The outside portion 2320 may be configured to be received within an interior cavity 2195 of a shell 2100 adjacent to an opening 2125 and a seal 1400. The outside portion 2320 may be configured to be secured to the interior cavity 2195 using a medical grade adhesive. The shell 2100 and the first disinfectant swab 2300 may be configured to retain the first disinfectant swab 2300 during insertion and withdrawal of a drainage spigot 3010. The inside portion 2310 may be generally cylindrical and may have a diameter less than or equal to a diameter of an exterior surface 3040 of a drainage spigot 3010. More specifically, the inside portion 2310 may have a diameter between 8 mm and 10 mm, preferably 9 mm. The length 2330 may be configured so that the first disinfectant swab 2300 is situated within the interior cavity 2195 and does not extend beyond the opening 2125.

Figures 10A, 10B, 10C:
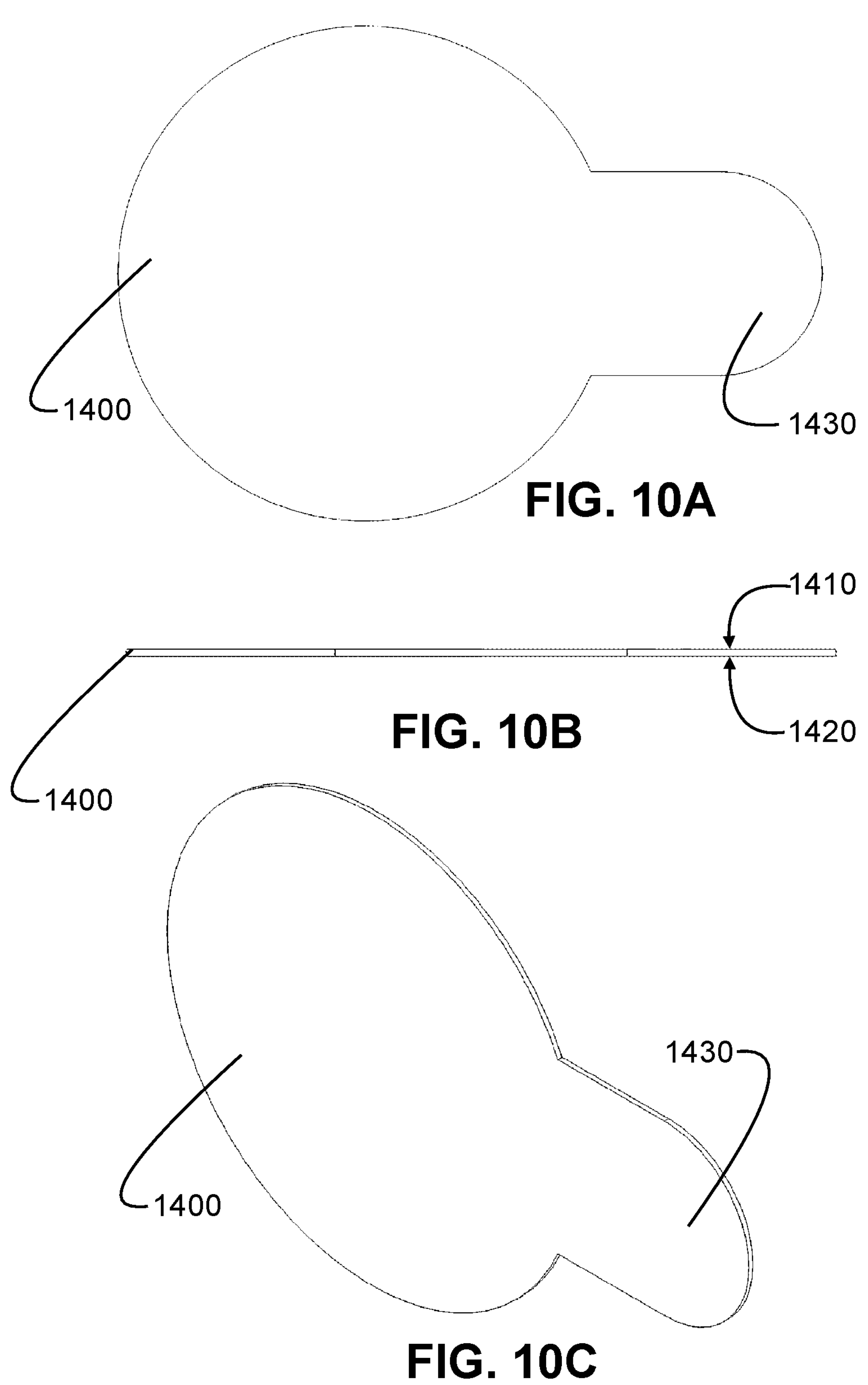
FIG. 10A is a top view of a seal of a drainage spigot guard according to an embodiment.
FIG. 10B is a side view of the seal of FIG. 10A.
FIG. 10C is a perspective view of the seal of FIG. 10A.

FIG. 10A is a top view of a seal 1400 of a drainage spigot guard 1000 and/or a drainage spigot guard 2000 according to an embodiment. FIG. 10B is a side view of the seal 1400 and FIG. 10C is a perspective view of the seal 1400. The seal 1400 may be configured to provide a sterile barrier and a moisture barrier for the interior cavity 1195 of the shell 1100, a first disinfectant swab 1300, and a second disinfectant swab 1200. Alternatively, the seal 1400 may be configured to provide a sterile barrier and a moisture barrier for the interior cavity 2195 of the shell 2100, a first disinfectant swab 2300, and a second disinfectant swab 2200.

The seal 1400 may be manufactured from metallic foil, plastic, silicone, rubber, paper, Tyvek, combinations thereof, and/or any other suitable sealing material. The seal 1400 may have an inner surface 1410, an outer surface 1420 and a pull tab 1430. The inner surface 1410 may be configured to attached to a flange 1130 of drainage spigot guard 1000 and/or a flange 2130 of a drainage spigot guard 2000. The inner surface 1410 may be attached using an adhesive, thermal bonding, or other suitable process. The outer surface 1420 may be configured to receive printing or other markings to identify the device, manufacturer, size, lot number, etc. The pull tab 1430 may be configured to extend beyond the flange 1130 and/or flange 2130. The pull tab 1430 may be further configured to allow a user to grip the seal 1400 and apply a force to disengage the seal 1400 from the shell 1100 and/or shell 2100.

Figure 11:
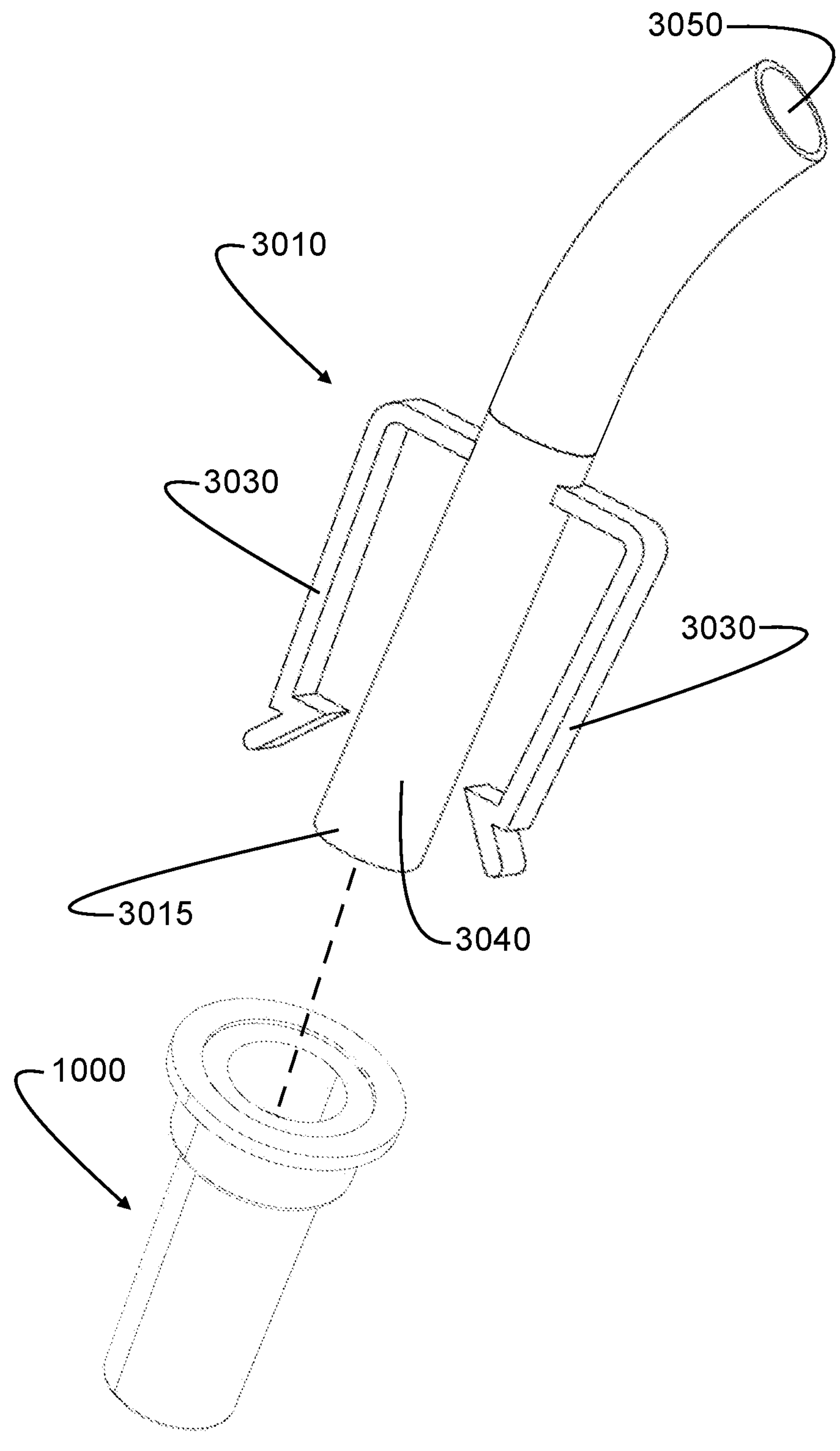
FIG. 11 is a perspective view of a drainage spigot and a drainage spigot guard according to an embodiment.

FIG. 11 is a perspective view of a drainage spigot 3010 and a drainage spigot guard 1000 according to an embodiment. The drainage spigot 3010 may include a spigot distal end 3015, locking arms 3030, an exterior surface 3040, and an interior surface 3050. The drainage spigot 3010 may be attached to a urinary catheter bag 3000 and may be configured to facilitate drainage of the urinary catheter bag 3000 by allowing liquid to flow from the urinary catheter bag 3000 through the interior surface 3050 into a collection vessel. The drainage spigot guard 1000 may be configured to receive the spigot distal end 3015 of the drainage spigot 3010 within the interior cavity 1195. The drainage spigot guard 1000 may further be configured so that during insertion of the drainage spigot 3010 into the interior cavity 1195 of the drainage spigot guard 1000, the spigot distal end 3015 engages the first disinfectant swab 1300 and the second disinfectant swab 1200 before the spigot distal end 3015 reaches the distal end 1110 of the shell 1100 of the drainage spigot guard 1000.

The drainage spigot guard 1000 may further be configured so that during insertion of the drainage spigot 3010 into the interior cavity 1195 of the drainage spigot guard 1000, the spigot distal end 3015 engages the first disinfectant swab 1300 and the second disinfectant swab 1200 before the movement of the drainage spigot guard 1000 is prevented by the locking arms 3030 of the drainage spigot 3010.

Figure 12:
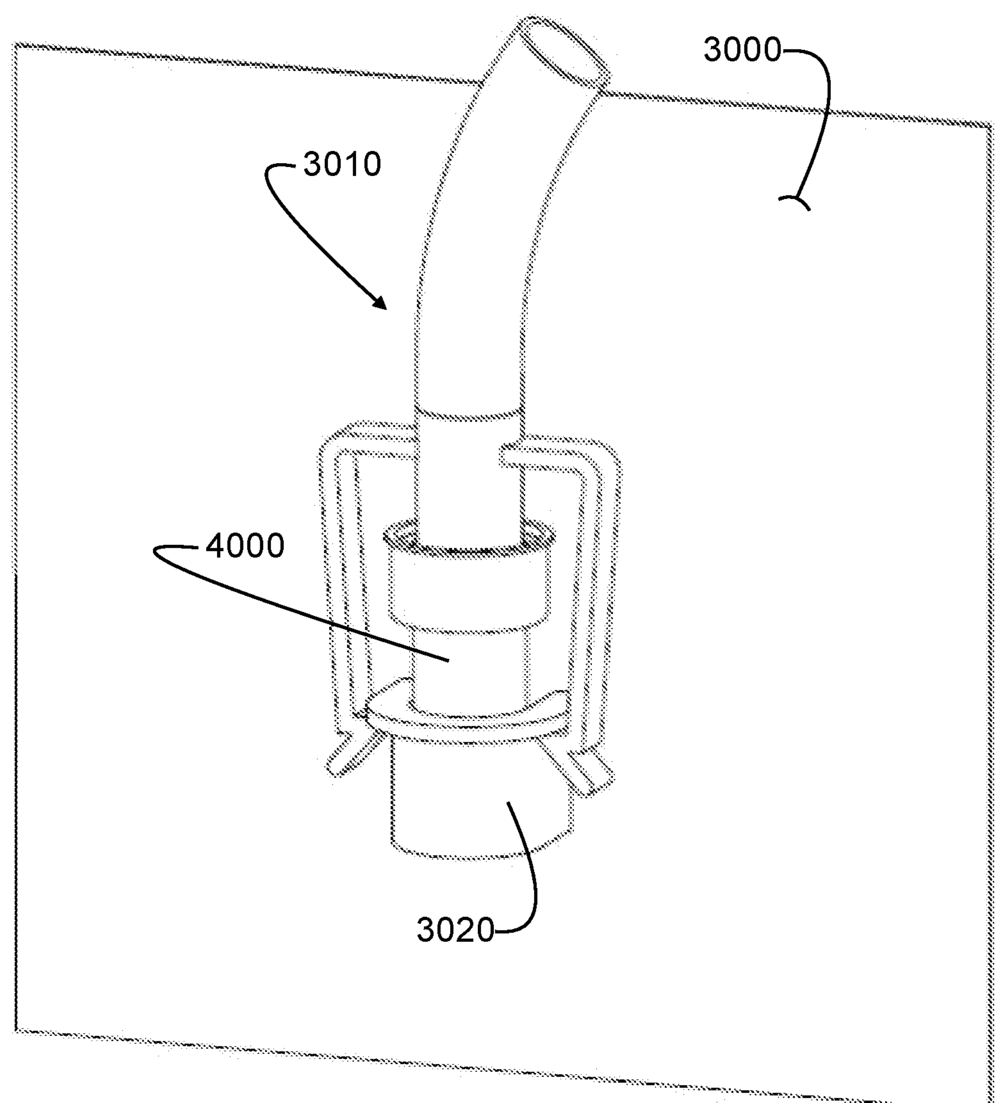
FIG. 12 is a perspective view of a portion of a urinary catheter bag with a spigot retainer, a drainage spigot and a drainage spigot guard according to an embodiment.
Figure 13:
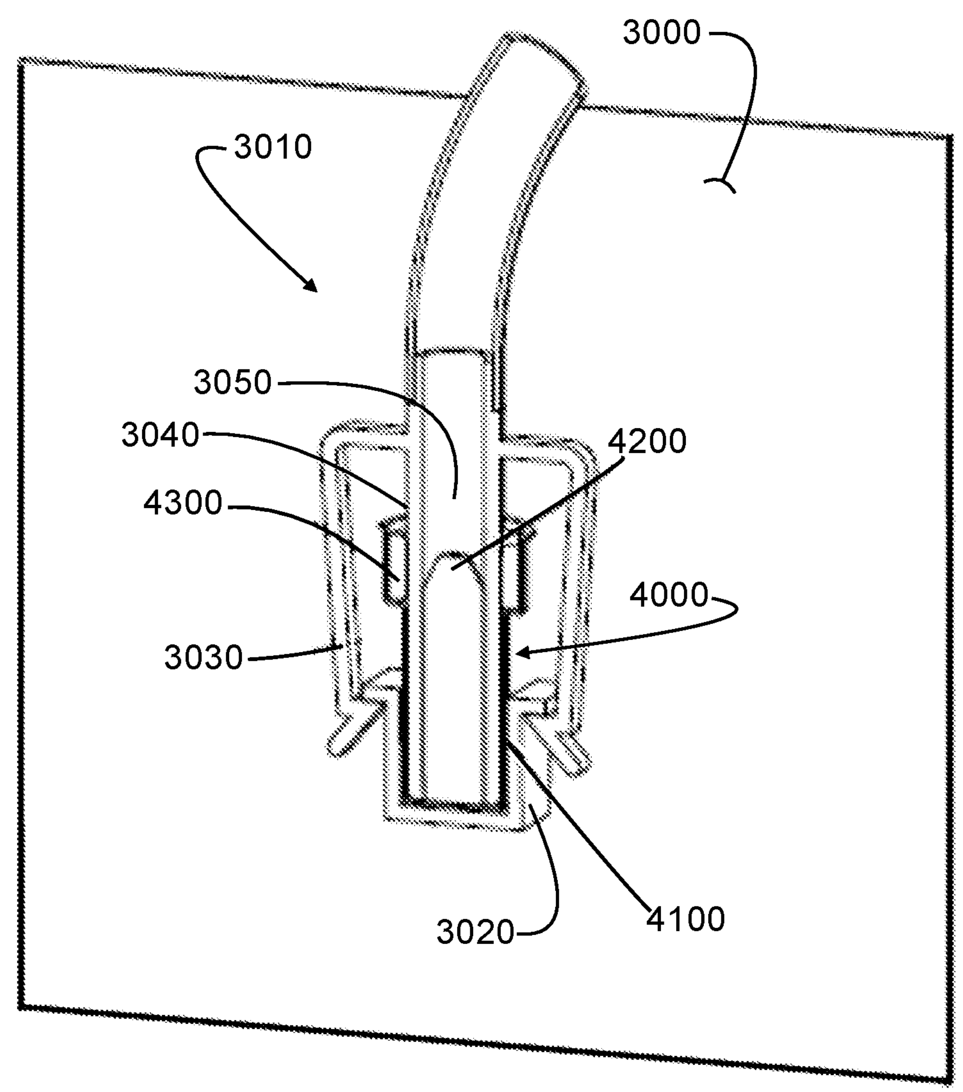
FIG. 13 is a perspective section view of the urinary catheter bag with the spigot retainer, the drainage spigot and the drainage spigot guard of FIG. 12.
Figure 14A:
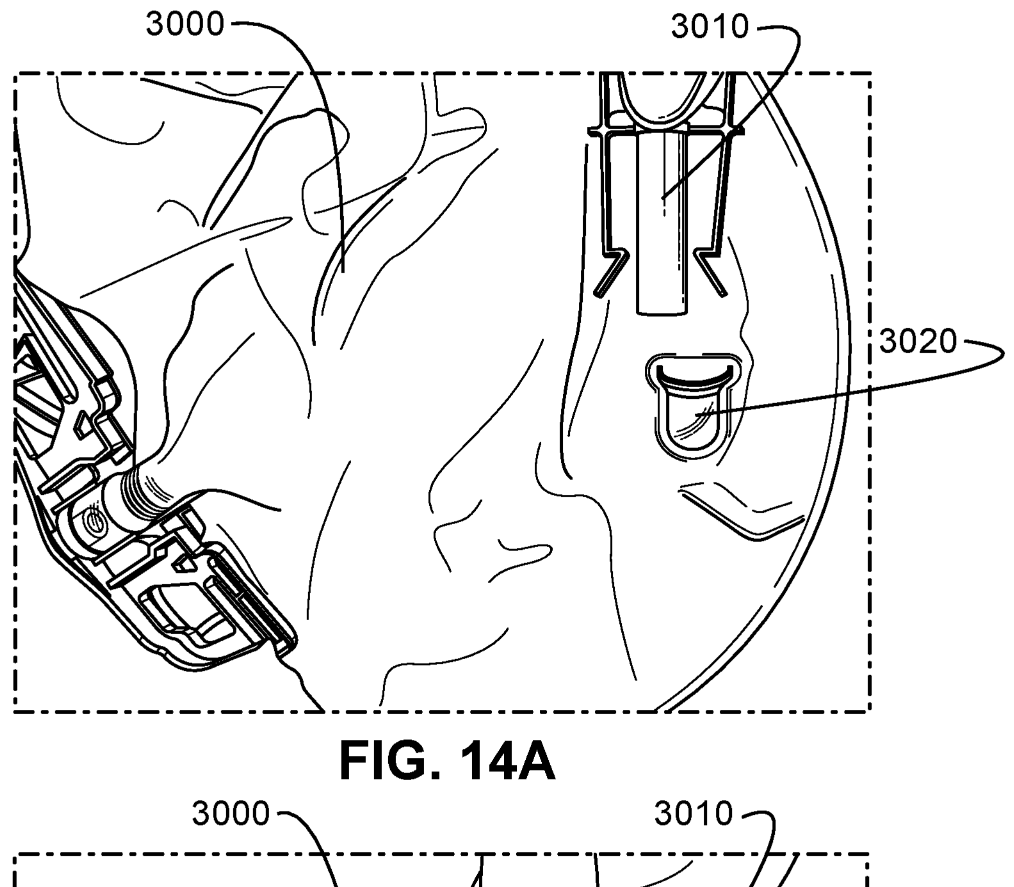
FIG. 14A is a perspective view of a step in a method for securing a drainage spigot guard to a drainage spigot according to an embodiment.
Figure 14B:
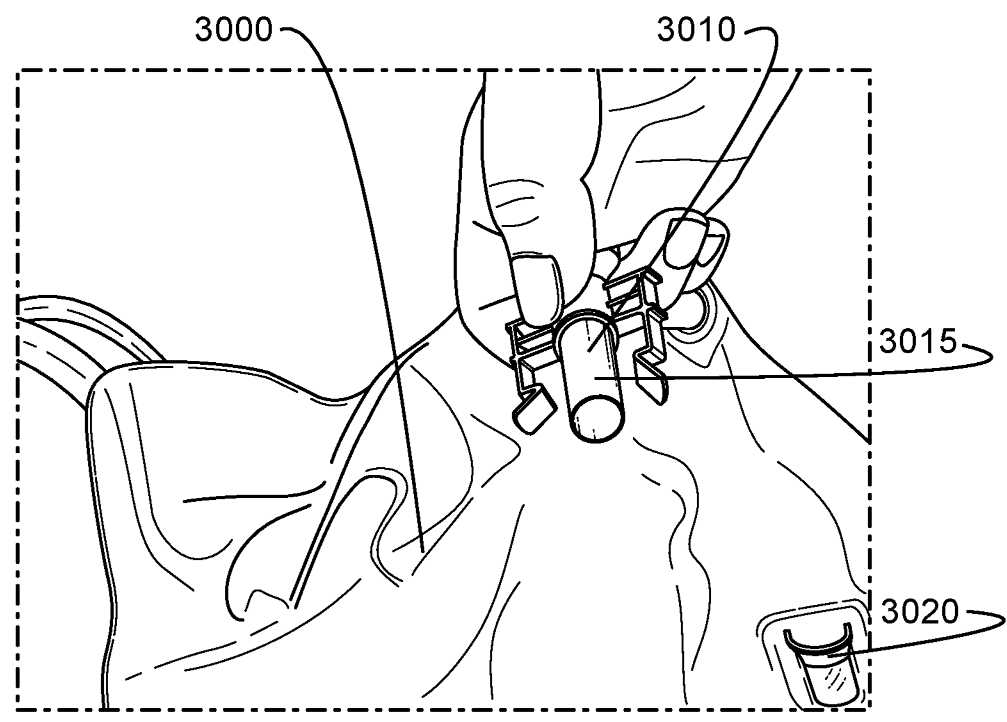
FIG. 14B is a perspective view of a step in a method for securing a drainage spigot guard to a drainage spigot according to an embodiment.
Figure 15A:
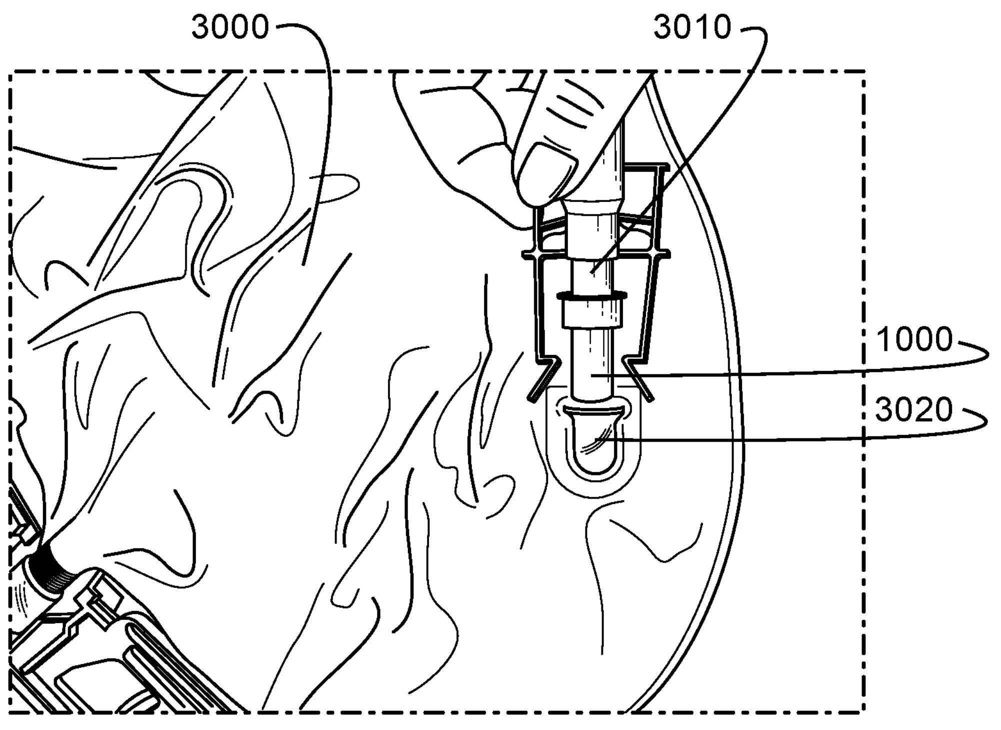
FIG. 15A is a perspective view of a step in a method for securing a drainage spigot guard to a drainage spigot according to an embodiment.
Figure 15B:
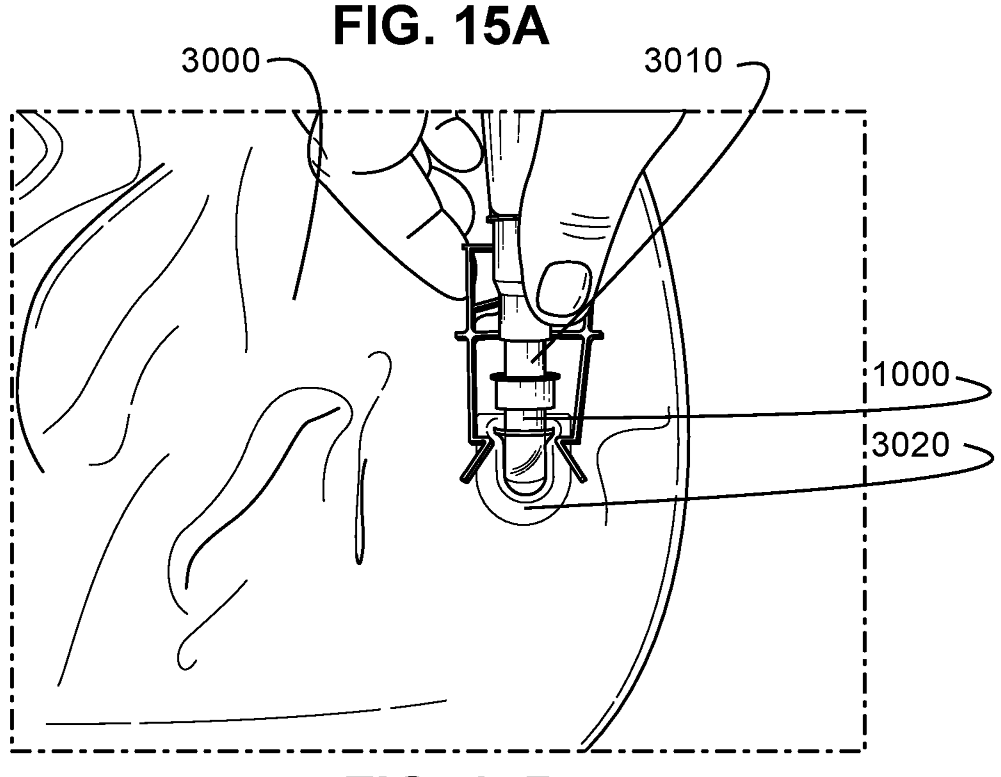
FIG. 15B is a perspective view of a step in a method for securing a drainage spigot guard to a drainage spigot according to an embodiment.

FIG. 12 is a perspective view of a portion of a urinary catheter bag 3000 with a spigot retainer 3020, a drainage spigot 3010 and a drainage spigot guard 4000 according to an embodiment. FIG. 13 is a perspective section view of the urinary catheter bag 3000 with the spigot retainer 3020, the drainage spigot 3010 and the drainage spigot guard 4000. The drainage spigot guard 4000 may include a shell 4100, a second disinfectant swab 4200, and a first disinfectant swab 4300. The drainage spigot guard 4000 may include similar functions and features previously described for the drainage spigot guard 1000 and/or the drainage spigot guard 2000.

The drainage spigot guard 4000 may include a shell 4100 configured to be received within the spigot retainer 3020 on a urinary catheter bag 3000 attached to the drainage spigot 3010. The drainage spigot guard 4000 may further be configured to allow the locking arms 3030 of the drainage spigot 3010 to engage the spigot retainer 3020 when the drainage spigot guard 4000 is received within the spigot retainer 3020.

The shell 1100 of the drainage spigot guard 1000, may be formed of silicone. However, in other embodiments the shell 1100 may be formed of other materials such as plastic, foil or and/or other packaging material. The shell 1100 may be configured with draft angles to facilitate injection molding. The draft angles may be between 0.5° and 3° per side.

FIG. 14A, FIG. 14B, FIG. 15A, and FIG. 15B are a perspective views of a step in a method for securing a drainage spigot guard 1000 to a drainage spigot 3010 according to an embodiment. An exemplary method of use of a drainage spigot guard 1000 may relate closely to its form and function. The drainage spigot guard 1000, configured to disinfect and guard a drainage spigot 3010, may comprise a first disinfectant swab 1300 and a second disinfectant swab 1200.

FIG. 14A, FIG. 14B, FIG. 15A, and FIG. 15B illustrate one exemplary method for securing a drainage spigot guard 1000 to a drainage spigot 3010 according to an embodiment. An exemplary method of securing a drainage spigot guard 1000 to a drainage spigot 3010 may include the following steps:

1. Disengage a drainage spigot from a spigot retainer attached to a urinary catheter;
2. Drain urinary catheter bag into an appropriate receptacle;
3. Advance spigot distal end of drainage spigot into interior cavity of a drainage spigot guard until drainage spigot is fully seated within the drainage spigot guard;
4. Advance drainage spigot with drainage spigot guard into the spigot retainer until the locking arms of the drainage spigot engage the spigot retainer.

The drainage spigot guard 1000 may be configured as a single use sterile device and may be discarded when removed from a drainage spigot 3010. The drainage spigot guard may be configured for home users with a leg bag urinary catheter. Each day a catheter portion may be separated from the leg bag urinary catheter so that a night bag urinary catheter may be connected. The exchange in type of bag may occur daily and the drainage spigot guard 1000 may cover and protect both open ends (catheter and bag tubing) for this process. The drainage spigot guard 1000 on the unused collection bag may stay in place until the exchange is made again to either a leg bag urinary catheter or night bag urinary catheter for cleanse and bacterial protection. The drainage spigot guard 1000 may be configured to cover and protect a spigot of a catheter that is temporarily not in use.

Those of skill in the art will recognize that this is only one of many potential methods that may be used to secure a drainage spigot guard 1000 to a drainage spigot 3010 and disinfect a drainage spigot 3010. In alternative embodiments, different methods may be used to secure a drainage spigot guard 1000 to a drainage spigot 3010 and disinfect a drainage spigot 3010. Further, the method set forth in FIG. 14A, FIG. 14B, FIG. 15A, and FIG. 15B may be used to secure other drainage spigot guards besides those specifically disclosed herein.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, instruments, and methods disclosed herein.

What is claimed is:

1. A catheter drainage spigot disinfecting guard configured to disinfect a catheter spigot having an exterior surface and an interior lumen having an interior surface of a urinary catheter, the drainage spigot disinfecting guard comprising:

a shell comprising:

an interior cavity shaped to receive the catheter spigot;

a first disinfectant swab within the interior cavity; and a second disinfectant swab within the interior cavity;

wherein:

the first disinfectant swab is annular in shape and is configured and positioned to disinfect the exterior surface of the catheter spigot in response to insertion of the spigot into the interior cavity;

the second disinfectant swab is configured and positioned to disinfect the interior surface of the interior lumen of the catheter spigot in response to insertion of the spigot into the interior cavity;

the shell further comprises an exterior shape configured to be received within a spigot retainer on a urinary catheter bag attached to the drainage spigot;

the first disinfectant swab terminates substantially short of a distal end of the interior cavity; and the second disinfectant swab terminates substantially short of the termination of the first disinfectant swab.

2. The drainage spigot guard of claim 1, wherein a proximal exterior diameter at a proximal end of the shell is larger than a distal exterior diameter at a distal end of the shell.

3. The drainage spigot guard of claim 1, wherein the shell further comprises an opening and a seal positioned to cover the opening.

4. The drainage spigot guard of claim 1, wherein a proximal diameter at a proximal end of the first disinfectant swab is larger than a distal diameter at a distal end of the first disinfectant swab.

5. The drainage spigot guard of claim 1, wherein the shell is configured to be received in a spigot retainer of a urinary catheter bag such that, with the shell on a spigot, locking arms secure the spigot to the spigot retainer.

6. A catheter drainage spigot disinfecting guard configured to disinfect a catheter spigot having an exterior surface and an interior lumen having an interior surface of a urinary catheter, the drainage spigot disinfecting guard comprising:

a shell comprising an interior cavity shaped to receive the catheter spigot;

a first disinfectant swab within the interior cavity; and a second disinfectant swab within the interior cavity; wherein:

the first disinfectant swab is annular in shape and is configured and positioned to disinfect the exterior surface the catheter spigot in response to insertion of the spigot into the interior cavity;

the second disinfectant swab is configured and positioned to disinfect the interior surface of the interior lumen of the catheter spigot in response to insertion of the spigot into the interior cavity;

the first disinfectant swab terminates substantially short of a distal end of the interior cavity; and the second disinfectant swab terminates substantially short of the termination of the first disinfectant swab.

7. The drainage spigot guard of claim 6, wherein the shell further comprises an opening and a seal positioned to cover the opening.

8. The drainage spigot guard of claim 6, wherein the second disinfectant swab is cylindrical in shape.

9. The drainage spigot guard of claim 6, wherein a proximal exterior diameter at a proximal end of the shell is larger than a distal exterior diameter at a distal end of the shell.

10. The drainage spigot guard of claim 6, wherein the second disinfectant swab comprises one of an inside portion configured to receive a post formed in the shell, and a stem configured to be received in a recess formed in the shell.

11. The drainage spigot guard of claim 6, wherein a proximal diameter at a proximal end of the second disinfectant swab is larger than a distal diameter at a distal end of the second disinfectant swab.

12. A catheter drainage spigot disinfecting guard configured to disinfect a catheter spigot having an exterior surface and an interior lumen having an interior surface of a urinary catheter, the drainage spigot disinfecting guard comprising:

a shell comprising:

an opening; and an interior cavity, accessible through the opening and shaped to receive the catheter spigot;

a seal positioned to cover the opening;

a first disinfectant swab within the interior cavity, adjacent to the opening and the seal; and a second disinfectant swab within the interior cavity; wherein:

the first disinfectant swab is annular in shape and is configured and positioned to disinfect the exterior surface at least part of the catheter spigot in response to insertion of the spigot into the interior cavity;

the second disinfectant swab is configured and positioned to disinfect the interior surface of the interior lumen of the catheter spigot in response to insertion of the spigot into the interior cavity;

the first disinfectant swab terminates substantially short of a distal end of the interior cavity; and the second disinfectant swab terminates substantially short of the termination of the first disinfectant swab.

13. The drainage spigot guard of claim 12, wherein the seal comprises a pull tab.

14. The drainage spigot guard of claim 12, wherein the shell further comprises a flange at a proximal end to facilitate attachment of the seal.

* * * * *